United States Patent [19]

Gurusamy

[11] Patent Number: 4,996,355

[45] Date of Patent: Feb. 26, 1991

[54] NOVEL INTERMEDIATES FOR THE PRODUCTION OF 2,4,5-TRIFLUOROBENZOYL FLUORIDE

[75] Inventor: Narayanasamy Gurusamy, Ballwin, Mo.

[73] Assignee: Mallinckrodt, Inc., St. Louis, Mo.

[21] Appl. No.: 338,162

[22] Filed: Apr. 14, 1989

[51] Int. Cl.$^5$ ............................................. C07C 63/04
[52] U.S. Cl. ................................... 562/493; 562/849; 562/840
[58] Field of Search ..................... 562/840, 849, 493

[56] References Cited

U.S. PATENT DOCUMENTS

| | | | |
|---|---|---|---|
| 3,290,353 | 12/1966 | Battershell | 562/840 |
| 3,816,526 | 6/1974 | Jurewicz et al. | 562/840 |
| 4,439,620 | 3/1984 | Klauke et al. | 568/437 |
| 4,762,831 | 8/1988 | Grohe et al | 514/230.2 |

FOREIGN PATENT DOCUMENTS

| | | |
|---|---|---|
| 1242742 | 10/1988 | Canada . |
| 0309789 | 4/1989 | European Pat. Off. . |
| 3420796 | 12/1985 | Fed. Rep. of Germany . |

OTHER PUBLICATIONS

Chu, D., J. Heterocyclic Chem. 22:1033 (1985).
Chu, et al., J. Med. Chem., 28:1558 (1985).
Yakobson, et al., Zh. Obshch. Khim. 32:3131 (1962).
Morrison & Boyd, Organic Chemistry, 3d Ed. (Allyn & Bacon, Inc., Boston, Mass.), 1973.
De Graw, et al., J. Chem. Eng. Data 13:587 (1968).
Sugawara et al., Kogyo Kagaku Zasshi, vol. 73, No. 5, pp. 972–979 (1970).

*Primary Examiner*—Paul J. Killos
*Attorney, Agent, or Firm*—Rothwell, Figg, Ernst & Kurz

[57] ABSTRACT

The present invention comprises compounds of the formulas:

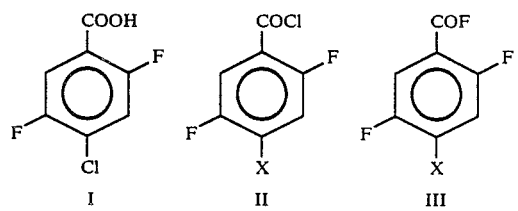

wherein X is Cl or Br.

These compounds are useful as intermediaries for the production of 2,4,5-trifluorobenzoic acid and 2,4,5-trifluorobenzoyl fluoride.

7 Claims, No Drawings

NOVEL INTERMEDIATES FOR THE PRODUCTION OF 2,4,5-TRIFLUOROBENZOYL FLUORIDE

FIELD OF THE INVENTION

The present invention relates to novel 4-chloro-2,5-difluorobenzoic acid, novel 2,5-difluoro-4-halobenzoyl chloride and novel 2,5-difluoro-4-halobenzoyl fluoride, methods for the manufacture thereof, and conversions of acid chloride and fluoride into 2,4,5-trifluorobenzoyl fluoride.

BACKGROUND OF THE INVENTION

The compound 2,4,5-trifluorobenzoic acid is a valuable intermediate in the production of fluoroquinolone compounds useful as antibacterial pharmaceuticals, as described in U.S. Pat. No. 4,762,831, or as an intermediate in the production of trans-4-(trans-4'-alkyl cyclohexyl) cyclohexyl 2,4,5-trifluorobenzoates, as described in JP 58/150543. The compound 2,4,5-trifluorobenzoyl fluoride is another useful intermediate for the production of antibacterial pharmaceuticals. This compound is described in EP 164,619. Trihaloaromatic-ketones, and in particular 2,4,5-trihaloacetophenones, also are useful intermediates in the synthesis of fluoroquinolone antibacterials. Chu, D., *J. Heterocyclic Chem.* 22:1033 (1985). The literature, however, provides few methods for the preparation of these intermediates or other intermediates which could be used for the production of antibacterial pharmaceuticals.

There is a need in the art for efficient methods of making these compounds and for the discovery of intermediates useful for making these compounds.

SUMMARY OF THE INVENTION

The present invention comprises compounds of the following formulas:

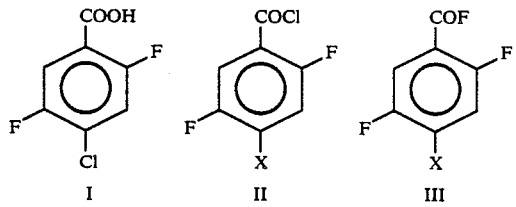

wherein X is Cl or Br.

These compounds are useful as intermediates for the production of 2,4,5-trifluorobenzoic acid, which is an intermediate for the preparation of antibacterial agents.

DETAILED DESCRIPTION OF THE INVENTION

The novel compounds of this invention may be represented by the following chemical structures:

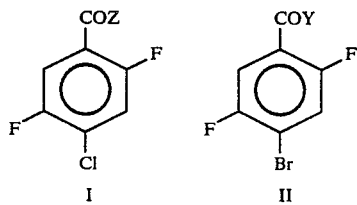

wherein Z is OH, Cl, or F, and Y is Cl or F.

The compound of formula I when Z is OH is produced by reacting a trihaloacetophenone with a metal hypohalite obtained from a halogen and a metal hydroxide or from other sources. The halogen preferably is chlorine, bromine or iodine, and the preferred trihaloacetophenone is 4-chloro-2,5-difluoroacetophenone. The compound produced is 4-chloro-2,5-difluorobenzoic acid.

The trihaloacetophenone which is used as the starting material may be produced by several methods. One process for synthesizing trihaloacetophenones has been reported by Yakobson et al. in *Zh. Obshch. Khim.* 32:3131 (1962). These authors teach synthesizing the desired compounds from 1,2,4-trihalobenzenes and acetic anhydride. Specifically, they teach that the acylation of a 1,2,4-trihalobenzene desirably is carried out in a medium of that trihalobenzene with 0.4 g/mole of acetic anhydride in the presence of $AlCl_3$ at 90°–100° C. and that increasing the amount of anhydride or the use of a solvent decreases the yield of acetophenone. In such an acylation, the product yield is based upon the amount of acetic anhydride and has been found to be in the range of 22–48%. The method also requires a large excess (approximately 3 molar excess) of the starting trihalobenzene.

A preferred method for producing trihaloacetophenones for use in the process of this invention for synthesizing novel intermediates involves reacting a 1,2,4-trihaloaromatic compound with an acyl halide compound in the presence of a catalyst to produce the desired trihaloacetophenones. This reaction is disclosed in Applicant's U.S. patent application entitled "Preparation of 2,5-difluoro-4-haloaromatic Ketones", Ser. No. 300,837 filed Jan. 24, 1989.

The trihaloacetophenone produced by one of these methods then may be used to produce the novel 4-chloro-2,5-difluorobenzoic acid of the present invention.

The starting material for the production of the 4-chloro-2,5-difluorobenzoic acid preferably is 4-chloro-2,5-difluoroacetophenone produced by one of the methods described above. The haloacetophenone is reacted with a metal hypohalite obtained from a halogen in a metal hydroxide solution or from other sources to produce a 4-chloro-2,5-difluorobenzoic acid. The metal hydroxide may be NaOH or KOH. The halogen may be chlorine, bromine, or iodine. The preferred metal hypohalite for use in this reaction is sodium hypohalite. This reaction proceeds as follows:

This reaction is a haloform reaction wherein the reactant is actually MOX, which oxidizes the ketone to the acid and produces $CHX_3$. The haloform reaction is known in the art and is described in Morrison & Boyd, *Organic Chemistry*, 3d Ed., Section 16.11, page 537.

This reaction should be carried out in water. The reaction generally takes from about 2 hours to about 18 hours. The reaction may be carried out at between about 0° C. and about 120° C. The reaction preferably is carried out at temperatures between about 25° C. and about 80° C.

When the starting material for the reaction is 4-chloro-2,5-difluoroacetophenone, the resulting compound is 4-chloro-2,5-difluorobenzoic acid, which was analyzed to determine physical properties and the structure. The melting point was 154–156° C.

This halobenzoic acid can be used to produce other useful compounds, leading to the production of 2,4,5-trifluorobenzoic acid. The 4-chloro-2,5-difluorobenzoic acid may also be useful as a substitute for 2,4,5-trifluorobenzoic acid in the production of fluoroquinolones since the 2 and 4 position halogens are removed in fluoroquinolone production. The 4-chloro-2,5-difluorobenzoic acid or other similar benzoic acids, such as 4-bromo-2,5-difluorobenzoic acid, may be used to produce other intermediates, for example, by carrying out the following reaction to obtain novel 2,5-difluoro-4-halobenzoyl chlorides:

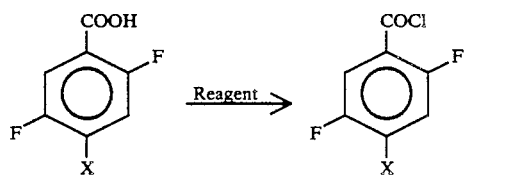

C

The conversion of benzoic acids to benzoyl chloride is known in the art and the reagent used to carry out the reaction may be thionyl chloride, phosphorus trichloride or phosphorus pentachloride. Morrison and Boyd, *Organic Chemistry*, 3d Edition, Section 18.15, page 601. The preferred reagent for this process is thionyl chloride. Generally, an excess of the reagent will be used to carry out the reaction. The amount of 2,5-difluoro-4-halobenzoic acid and the amount of reagent used normally will be in a ratio of between about 1:1 and about 1:10.

The resulting novel compound is either 4-chloro-2,5-difluorobenzoyl chloride or 4-bromo-2,5-difluorobenzoyl chloride. This novel compound may be further purified, if desired.

The novel benzoylchlorides also are intermediates and may be further reacted to produce novel 2,5-difluoro-4-halobenzoyl fluorides and 2,4,5-trifluorobenzoic acid as follows:

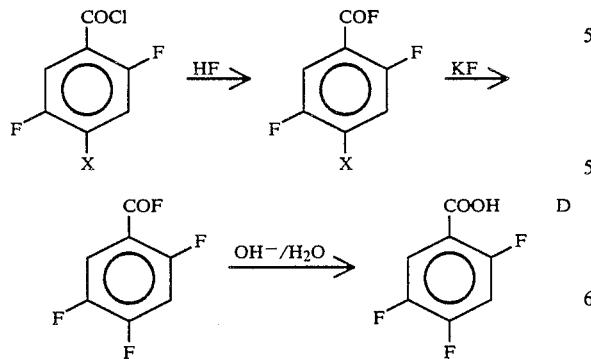

D

In this reaction, the 2,5-difluoro-4-halobenzoyl chlorides first are reacted with anhydrous hydrogen fluoride to produce the novel 2,5-difluoro-4-halobenzoyl fluorides. An excess of the hydrogen fluoride preferably is used.

The 2,5-difluoro-4-halobenzoylfluorides then are reacted with such agents as cesium fluoride, potassium fluoride, and the like, optionally using a phase transfer catalyst, to produce 2,4,5-trifluorobenzoyl fluorides through a halogen exchange reaction. The preferred agent for carrying out this reaction is potassium fluoride (shown above in reaction D). The halogen substitution usually is carried out in a neat reaction at a temperature range of from 120° C. to about 210° C. using a phase transfer catalyst such as polyethylene glycol, n-alkyl pyridinium salts or tetralkyl ammonium salts, e.g., tetramethyl ammonium chloride. Preferably, the reaction temperature ranges from about 150° C. to about 190° C. and the molar ratio of suitable agent, e.g., KF, is present in a molar ratio to the 2,5-difluoro-4-halobenzoyl fluoride of from 1:1 to 2:1 with a molar ratio of from 1.1:1 to 1.5:1 being preferred.

In the final step of the production of 2,4,5-trifluorobenzoic acid shown in D above, the 2,4,5-trifluorobenzoyl fluoride produced is hydrolyzed by methods known to those skilled in the art. One such method involves combining the 2,4,5-trifluorobenzoyl fluoride with an aqueous solution of sodium hydroxide and heating the mixture. The hot mixture is filtered and made acidic by addition of a mineral acid, e.g., HCl, in order to precipitate the desired product. The precipitated product of 2,4,5-trifluorobenzoic acid then is collected by conventional methods of filtration.

In a variation of the above-illustrated reaction, the 2,5-difluoro-4-halobenzoyl chloride may be reacted in a halogen substitution reaction to form 2,4,5-trifluorobenzoyl fluoride which is hydrolyzed to 2,4,5-trifluorobenzoic acid. The molar ratio of KF to 2,5-difluoro-4-halobenzoyl chloride ranges from about 2:1 to 4:1. This reaction will proceed as follows:

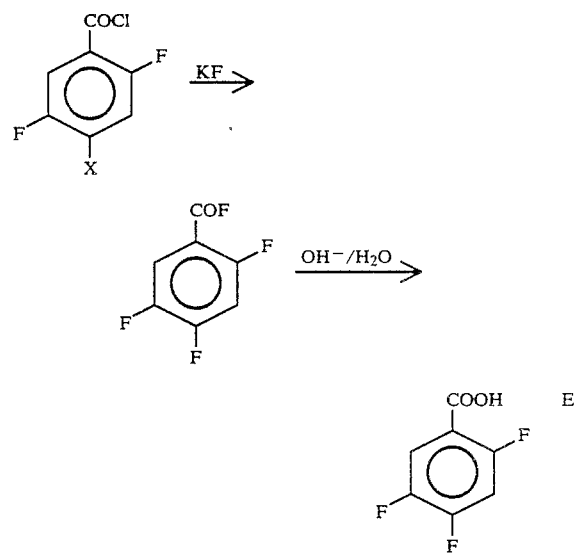

E

The following examples further illustrate the process of this invention, but are not meant to limit the scope of the invention in any way.

EXAMPLES

EXAMPLE 1

Preparation of 4-Chloro-2,5-difluorobenzoic Acid

A 3.6 liter aqueous solution containing 500 g (5.5 mole) of potassium hypochlorite and 115 g potassium hydroxide, was taken in a 5 liter, 3-necked round-bottomed flask equipped with a Trubore stirrer, a thermometer, an addition funnel and a water condenser. 228.5 g (1.2 mole) of 4'-chloro-2',5'-difluoroacetophenone was dissolved in 550 ml of chloride and the solution was slowly added to the flask via the addition funnel. The temperature was not allowed to exceed 40° C. After the addition was complete, the heterogeneous mixture was stirred vigorously at reflux (40° C.) for 18 hours.

The reaction mixture was cooled to room temperature and filtered. The solid was dried and then suspended in 2200 ml of water containing 120 ml of concentrated HCl. It was stirred, filtered, washed with water, and dried in an oven to a constant weight of 177 g. It had a melting point of 154.7° C. The $CH_2Cl_2$ layer was rotovapped to recover 30 g (13%) of the starting ketone, 4'-chloro-2',5'-difluoroacetophenone. The conversion of the ketone into acid was 87%. The yield of 4-chloro-2,5-difluorobenzoic acid was 88%.

EXAMPLE 2

The above reaction was repeated, cutting down the reflux time to 2 hours instead of 18 hours. The conversion was 79% and the yield of 4-chloro-2,5-difluorobenzoic acid was 83%.

EXAMPLE 3

Preparation of 4-chloro-2,5-difluorobenzoyl Chloride 38.5 g 4-chloro-2,5-difluorobenzoic acid (0.2 mole) was placed in a 250 mL, 3-necked roundbottom flask equipped with a magnetic stirbar, a thermometer, and a water-cooled condenser. 238 g thionyl chloride was added in one lot. The mixture was stirred and heated on a water bath. At about 58°-60° C. the solid dissolved with evolution of gas and formation of foam. The mixture was stirred and maintained at 60° C. until all the solid dissolved - about 30 minutes. It was then heated in a boiling water bath to reflux and held there for 2 hours.

The excess thionyl chloride was distilled out. The contents were cooled and then distilled under reduced pressure. The capillary GC analysis showed the distilled product to be 99.6% pure. The yield was 41.1 g, 98%.

EXAMPLE 4

Preparation of 4-chloro-2,5-difluorobenzoyl Fluoride 52.0 g anhydrous hydrogen fluoride was condensed in a 500-mL plastic container precooled in a dry ice-/acetone bath. 32.0 g 4-chloro-2,5-difluorobenzoyl chloride, prepared in Example 2, was added in one step with stirring. The acid chloride froze to a white solid. The container was removed from the bath and allowed to warm. When it reached approximately 10° C., the solid started to dissolve, giving off HCl and HF fumes. Stirring continued until gas evolution subsided at about room temperature. The container was warmed to about 40° C. in water bath and stirred to remove gases for about 30 minutes. 50 mL Freon 113 and 5 g sodium fluoride were added and the mixture stirred for 10 minutes. The contents were filtered through a suction flask.

The clear filtrate was evaporated on a rotovapor to get 28.8 g of a clear liquid having a 97.9% purity by GC analysis. The yield was 98.6%.

EXAMPLE 5

Preparation of 2,4,5-Trifluorobenzoyl Fluoride

Oven-dried and pulverized potassium fluoride (56 g) was added to 4-chloro-2,5-difluorobenzoyl fluoride (134 g) taken in a 500 ml 3-necked round-bottomed flask equipped with a Trubore stirrer, a thermometer and a water condenser topped with a T-connection leading to a mineral oil bubbler on one end and a nitrogen source on the other end. The nitrogen blanket was maintained during the reaction in order to exert back pressure. The suspension was stirred vigorously and heated up to 145° C. The phase transfer catalyst, N-neopentyl-4(4'-methylpiperidinyl) pyridinium chloride (0.5 g) was added and the reaction temperature was raised. Reflux of the contents started at about 172° C. and the stirring was continued. The catalyst was added in 0.5 g lots after 3 hours and 5 hours of reaction time. After stirring for 23 hours, the reaction mixture was cooled to room temperature and filtered. The filter cake was washed with Freon 113 (100 ml). The washings were combined with the filtrate and fractionally distilled under atmospheric pressure to get 88.5 g of 2,4,5-trifluorobenzoyl fluoride, having a b.p. of 155-156° C. The yield was 72%.

EXAMPLE 6

Preparation of 2,4,5-Trifluorobenzoyl Fluoride

Oven-dried and pulverized potassium fluoride (18 g) was added to 4-chloro-2,5-difluorobenzoyl chloride (26.4 g) taken in a 100 ml 3-necked round-bottomed flask equipped with a Trubore stirrer, a thermometer and a water condenser topped with calcium chloride guard tube. The suspension was stirred vigorously and heated up to 145° C. The phase transfer catalyst, N-(2-ethylhexyl)-4-(4'-methylpiperidinyl) pyridinium chloride (0.5 g) was added and the reaction temperature was raised to 180° C. The catalyst was added in 0.5 g lots after 3 hours and 19 hours of reaction time. After stirring for 23 hours, the reaction mixture was cooled to room temperature and filtered. The filter cake was washed with Freon 113 (100 ml). The washings were combined with the filtrate and rotovapped to get 11.2 g (50%) of 2,4,5-trifluorobenzoyl fluoride.

EXAMPLE 7

Preparation of 2,4,5-Trifluorobenzoic Acid

A 2 liter 3-necked round-bottomed flask equipped with a Trubore stirrer, a thermometer and a condenser, was charged with 500 ml of water and 42.4 g of sodium hydroxide pellets. The 2,4,5-trifluorobenzoyl fluoride (95 g) was added to it via a dropping funnel, maintaining the temperature below 30° C. The contents were stirred vigorously and heated on a hot water bath to get a clear solution which was diluted further by the addition of an additional 250 ml of hot water. The contents were stirred on the boiling water bath for a period of one hour. The clear solution was acidified to pH 1 with concentrated hydrochloric acid and cooled to get white crystalline solid which was filtered, washed with cold water and dried in an oven to a constant weight of 91 g (97.6%) of 2,4,5-trifluorobenzoic acid. It had a melting point of 97.2° C. The structure of the compound was supported by $^1H$, $^{13}C$, $^{19}F$ NMR as well as FTIR spectral data.

I claim:

1. A compound of the formula
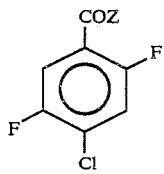
wherein Z is OH, Cl or F.
2. 4-Chloro-2,5-difluorobenzoic acid.
3. 4-Chloro-2,5-difluorobenzoyl chloride.
4. 4-Chloro-2,5-difluorobenzoyl fluoride.
5. A compound of the formula
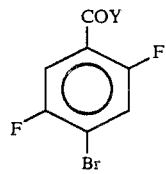
wherein Y is Cl or F.
6. 4-bromo-2,5-difluorobenzoyl chloride.
7. 4-bromo-2,5-difluorobenzoyl fluoride.
* * * * *

UNITED STATES PATENT AND TRADEMARK OFFICE
CERTIFICATE OF CORRECTION

PATENT NO. : 4,996,355

DATED : February 26, 1991

INVENTOR(S) : Gurusamy

It is certified that error appears in the above-identified patent and that said Letters Patent is hereby corrected as shown below:

Column 5, line 5, insert --methylene-- before chloride

Signed and Sealed this

Twentieth Day of October, 1992

Attest:

DOUGLAS B. COMER

Attesting Officer

Acting Commissioner of Patents and Trademarks